United States Patent [19]

Mills et al.

[11] Patent Number: 5,012,814
[45] Date of Patent: May 7, 1991

[54] IMPLANTABLE-DEFIBRILLATOR PULSE DETECTION-TRIGGERED ECG MONITORING METHOD AND APPARATUS

[75] Inventors: Gary N. Mills, Gladstone; Habib Homayoun, Aloha, both of Oreg.

[73] Assignee: Instromedix, Inc., Hillsboro, Oreg.

[21] Appl. No.: 433,753

[22] Filed: Nov. 9, 1989

[51] Int. Cl.$^5$ ............................................. A61N 1/37
[52] U.S. Cl. ................................ 128/691; 128/419 D; 364/413.06 LM
[58] Field of Search .................... 128/696, 697, 419 D; 364/413.06

[56] References Cited

U.S. PATENT DOCUMENTS

| | | | |
|---|---|---|---|
| 4,295,474 | 10/1981 | Fischell | 128/419 D |
| 4,457,315 | 7/1984 | Bennish | 128/704 |
| 4,506,677 | 3/1985 | Lambert | 128/697 |
| 4,532,935 | 8/1985 | Kelen | 128/697 |
| 4,596,255 | 6/1986 | Snell et al. | 128/697 |
| 4,653,022 | 3/1987 | Koro | 364/900 |
| 4,667,682 | 5/1987 | Ihlenfeld, III | 128/711 |
| 4,716,903 | 1/1988 | Hansen et al. | 128/419 PG |
| 4,791,936 | 12/1988 | Snell et al. | 128/697 |

Primary Examiner—William E. Kamm
Assistant Examiner—Scott M. Getzow
Attorney, Agent, or Firm—Kolisch, Hartwell, Dickinson, McCormack & Heuser

[57] ABSTRACT

Ambulatory ECG data monitoring and recording method and apparatus that selectively captures recorded data based upon the occurrence of a defibrillation pulse from an implantable cardioverter/defibrillator monitor (ICDM) device is described. The apparatus uses a single pair of skin electrodes to sample the ECG signal waveform and to monitor the voltage therebetween for the detection of a ICDM-produced pulse of characteristic amplitude and duration. ECG data are continuously stored in a scrolling buffer of limited depth. Detection of a defibrillation pulse is treated as a trigger event, prompting the continuation of ECG data storage only for a limited further period of time after which the present ECG data record is captured. The buffered data are marked by the occurrence of the defibrillation pulse that prompted their capture, so that the information stored for subsequent playback indicates the timing relationship therebetween. A new buffer is initialized and ECG data recording and defibrillation pulse detection continues. Selectively capture-stored and marked ECG data can be played back to a remote site for diagnosis of a relatively longterm, ambulatory cardiac patient monitoring and recording session. Optionally, the cardiac patient may manually trigger the capture-store of ECG data.

12 Claims, 3 Drawing Sheets

IMPLANTABLE-DEFIBRILLATOR PULSE DETECTION-TRIGGERED ECG MONITORING METHOD AND APPARATUS

BACKGROUND AND SUMMARY OF THE INVENTION

This invention relates generally to ambulatory heart monitoring method and apparatus. More specifically, it concerns ambulatory ECG data monitoring and recording method and apparatus having integral therewith implantable-defibrillator pulse detection means defining trigger events upon which ECG data are capture-stored for subsequent playback.

Implantable cardio-verter/defibrillator monitor (ICDM) devices are implanted in the chest cavities of heart patients for automatically pacing and, in the event of fibrillation, stimulating their hearts. Most ICDM devices perform no ECG data monitoring or recording function. The only ones known to do so must compress the ECG data, as storage capacity for ECG data within an implanted device is extremely limited, and/or must telemetrically communicate the ECG data in real time to an external recording device. The most advanced ambulatory ECG data recording and monitoring devices (such as that described in copending U.S. Pat. application Ser. No. 07/321,736, filed March 10, 1989, entitled "Improved Heart Data Monitoring Method and Apparatus", which issued Sept. 25, 1990 as U.S. Pat. No. 4,958,641 having a common assignee herewith), perform no ICDM pulse detection. The only one known to do so continuously monitors both ECG signal and ICDM pulse waveforms for recording them in analogue form on magnetic tape. None of the prior art devices provides long-term monitoring and selective recording of information regarding the pre-ICDM pulse condition that led to the production of a pulse by the ICDM device and the post-ICDM pulse cardiac response thereto.

Accordingly, it is a primary object of this invention to provide an ambulatory heart data monitoring and recording device capable of continuously monitoring and selectively recording ECG data based upon the monitoring of ICDM, or defibrillation, pulses.

Another object of the invention is to provide an ambulatory ECG data monitoring and recording device with ICDM pulse detection means for triggering the capture of ECG data related in time to the occurrence of the ICDM pulse.

Yet another object is to provide ambulatory apparatus having limited memory capacity with the capability of recording selectively ICDM pulse-pertinent ECG data over a long-term recording and monitoring session.

Still another important object of the invention is to provide for the monitoring and recording of ECG data and the detection of ICDM pulses by the use of a single pair of skin electrodes.

Another object is to provide a method of capturing ECG data based upon the occurrence of a ICDM pulse in such manner that the data and the occurrence are relatable in time, thereby facilitating diagnosis of the patient's pre- and post-ICDM pulse cardiac condition.

It is also an object of the invention to provide such method and apparatus in a lightweight, durable, low-cost product that is simple to use and which imposes few restrictions upon the ambulatory patient.

These and other objects of the invention will be understood in reference to the following detailed description of the preferred embodiment and method of the invention, and by reference to the accompanying drawings.

DETAILED DESCRIPTION OF THE PREFERRED EMBODIMENT

Figure 1:
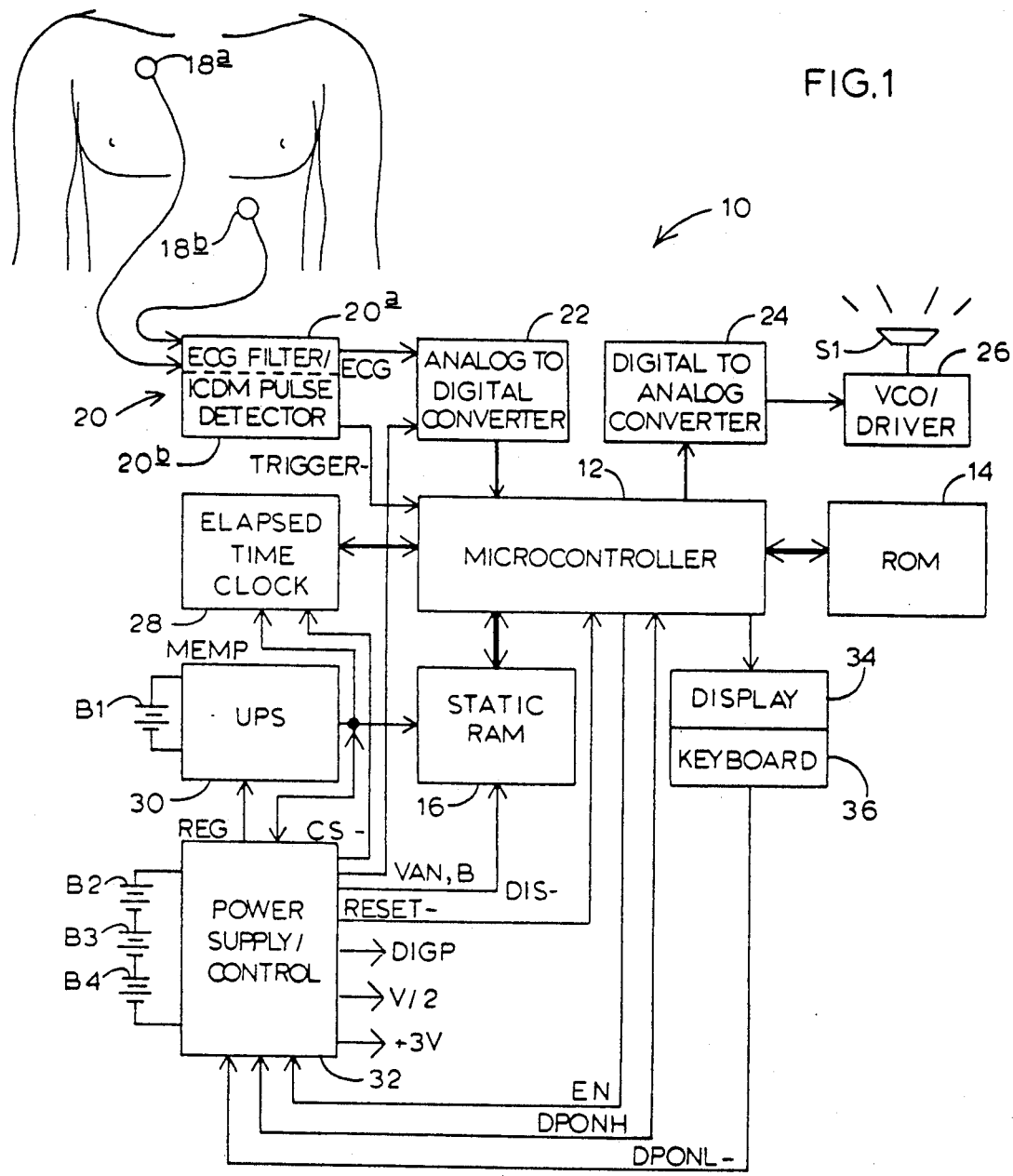
FIG. 1 is a simplified, schematic block diagram of the apparatus of the invention, made in accordance with its preferred embodiment.

Referring first to FIG. 1, a simplified, schematic block diagram of the apparatus of the invention, indicated generally at 10, is shown. In the interest of brevity and clarity, various details are intentionally omitted from FIG. 1, e.g. latches and drivers are not shown but will be understood by those skilled in the art to be required, depending upon the particular devices chosen to perform the required functions. Undisclosed hardware implementation details follow established design rules, and form no part of this invention. Signature conventions are used consistently herein to facilitate descriptions of signals and signal paths. Signatures consist of capitalized words or phrases that are believed to suggest a signal's function in the circuit being described. A signature having a hyphen (-) as a suffix will be understood to be low-active.

Apparatus 10 is a lightweight, ambulatory, battery-powered device that is capable of measuring, recording and transmitting (playing back) heart and ICDM performance information, or indicia, to a remotely located physician for diagnosis, with the information taking the form of digitized ECG signals and an indication of when, in timed relation thereto, defibrillation pulses produced by an ICDM occurred. It will be understood that ICDM-produced pulses are referred to herein interchangeably as ICDM, ICDM-produced and defibrillation pulses. Apparatus 10 is self-contained, requiring no external power, and conveniently can be carried upon the person of the patient. In its preferred embodiment, apparatus 10 can, for up to fourteen days, continuously monitor ECG data, and selectively capture-store, or semi-permanently record, ECG data that correspond to occurrences of ICDM-produced pulses from a ICDM implanted in the chest cavity of the cardiac patient wearing apparatus 10. Such a ICDM-produced pulse is treated by apparatus 10 as a trigger event, and each such pulse causes a capture-store of the patient's ECG data immediately therebefore and thereafter. Optionally, the patient can capture-store ECG data upon demand, if it is thought that a significant cardiac event, e.g. an arrhythmia or ischemia, is imminent, is occurring or has occurred.

Apparatus 10 includes computer means, or a microprocessor or microcontroller, 12; program storage means, or a read-only memory (ROM), 14; and semiconductor memory means or a semiconductor memory device for data storage, e.g. a static RAM, 16. In a manner that will be described below in reference to FIGS. 2 and 3, a program located in ROM 14 is executed by microcontroller 12 upon application of power via closure of a switch, and RAM 16 stores blocks of ECG data pertaining to the patient's cardiovascular performance as it relates to the performance of an implanted ICDM (which ICDM is not shown in FIG. 1, and forms no part of the present invention). ECG signals are monitored by conventional probes or electrodes, such as electrodes 18a, 18b, shown in FIG. 1 in the well-known "Lead II" position on a patient's chest and in operative contact with the patient's skin.

Probes 18a, 18b provide a differential, analog signal representative of the dynamically changing electrical field on the skin surface of the patient. This analog signal is conditioned by an ECG amplifier/filter circuit 20a of ECG/pulse monitor 20 to generate a conditioned, analog ECG signal representative of the patient's cardiography. A ICDM pulse monitor circuit 20b of ECG filter/ICDM pulse detector 20 produces a TRIGGER- signal upon detection of a pulse having predefined amplitude and frequency attributes characteristic of a ICDM-produced pulse. The ECG signal is converted (at a rate of approximately 109-Hz) by an analog-to-digital converter (ADC) 22 into successive eight-bit digital values, which are input to microcontroller 12 via one of its data ports. A digital-to-analog converter (DAC) 24 and a voltage controlled oscillator (VCO)/driver circuit 26 enable frequency-shift-keyed (FSK) and frequency-modulated (FM) tones to be generated via speaker S1 for data communication to a remote site, as by placing a telephone transmitter adjacent a small hole provided in the enclosure of apparatus 10. The TRIGGER- signal is monitored by microcontroller 12, as will be described in some detail below.

Referring still to FIG. 1, a programmable elapsed time clock 28 provides means for recording, with the ECG data, the total time that has elapsed from the moment when monitoring began, thus providing a relative indication of the time at which the reading was taken. As they must retain their otherwise volatile memory contents in the event of battery failure or excessive discharge, RAM 16 and clock 28 are powered by a backup, or uninterruptable, power supply (UPS) 30. This ensures that data are not lost when the power switch is turned off or when the primary power source is depleted.

Power supply means are provided in apparatus 10 by UPS 30 and power supply/control 32. DC power is supplied to UPS 30 by a single lithium battery B1, enabling UPS 30 to supply—without interruption and over the life of battery B1—a reduced level of unregulated voltage sufficient to sustain the potentially volatile data contents of RAM 16 and clock 28. Power supply/control 32 supplies RESET- to microcontroller 12, DIS- to RAM 16, CS- to clock 28, VAN and B to ADC 22, DIGP to certain of the remaining (mostly digital) circuitry, and +3V and V/2 to ECG filter/ICDM pulse detector 20 of apparatus 10. Power supply/control 32 also supplies REG to UPS 30 so that, should REG fall below a predetermined voltage level, UPS 30 continues without interruption to supply an unregulated, reduced DC voltage level to the volatile circuit elements. Alkaline batteries B2, B3, B4, which have a life of approximately fourteen days, are the primary source of DC power to power supply/control 32. A graphic liquid crystal display (LCD) 34 and a three-pushbutton keyboard 36 enable the physician or the patient to view selected parameters stored in ROM 14 or RAM 16 and, if desired, to change those stored in RAM 16. Closure of any of the pushbuttons of keyboard 36 produces a signal DPONL-, which is routed to power supply/control 32.

Figure 2:
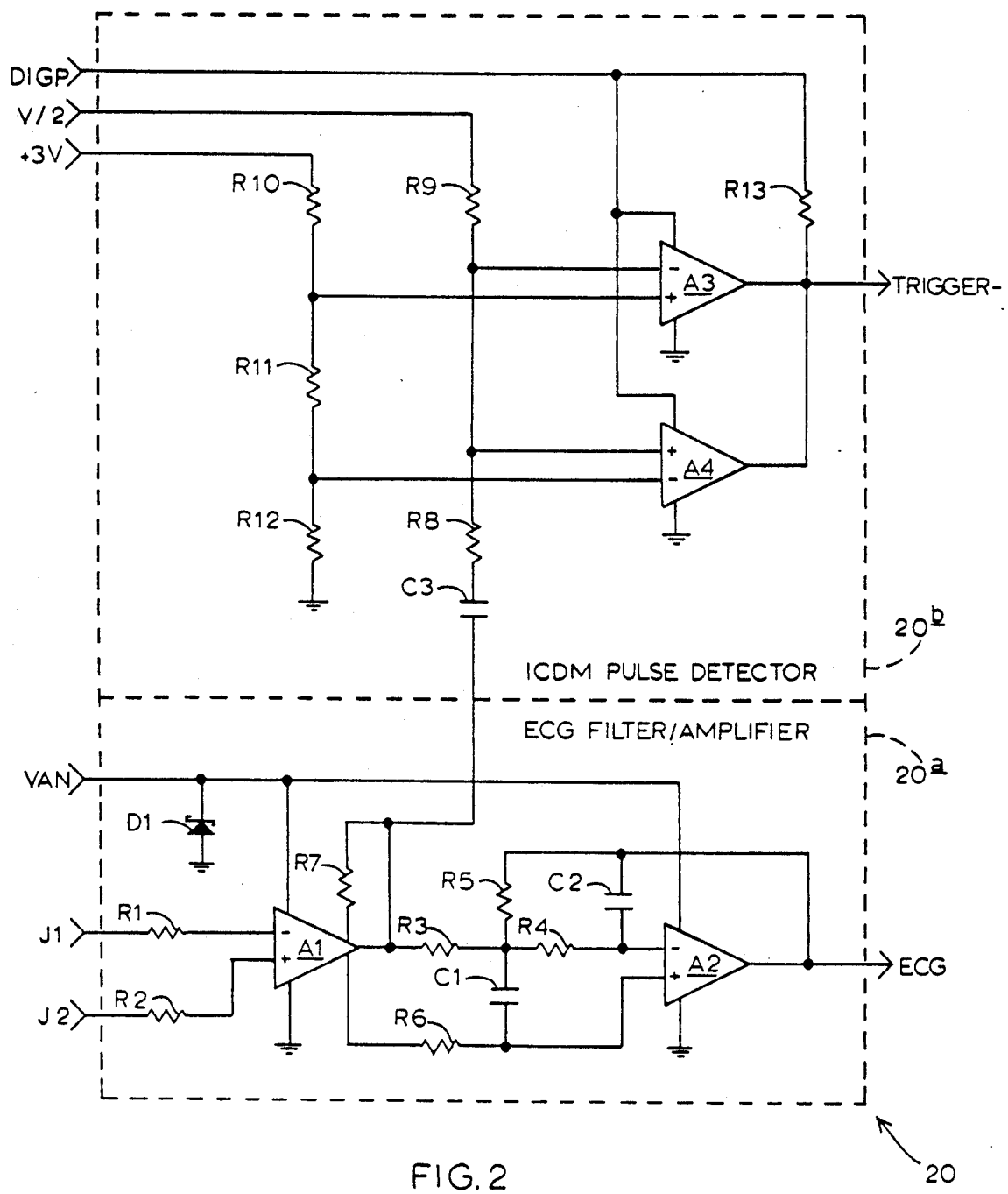
FIG. 2 is a detailed, schematic diagram of the ICDM pulse detection means of the apparatus of the invention.

Turning now to FIG. 2, ECG/pulse monitor 20 will be described in detail. ECG amplifier/filter circuit 20a includes input jack terminals J1, J2 connected in the operation of apparatus 10 to a pair of electrodes, such as electrodes 18a, 18b shown in FIG. 1. Signals present on J1, J2 pass through series 100-kΩ resistors R1, R2 to an amplifier A1 as shown. The output of amplifier A1 is filtered by resistors R3 through R5, capacitors C1 and C2 and amplifier A2. The reference voltage level for amplifier A1 is set by a resistor R6 and the gain of amplifier A1, which in the preferred embodiment is approximately four, is set by a resistor R7. In the preferred embodiment, the values of R3, R4, R5, R6, and R7 are 51-kΩ, 36-kΩ, 100-kΩ, 36-kΩ, and 36-kΩ, respectively. In the preferred embodiment, the values of capacitors C1 and C2 are 0.1-μF and 0.033-μF, respectively. In the preferred embodiment, the active, low-pass filter of ECG amplifier/filter 20a has its 3-db point at approximately 36-Hz and its 6-db point at approximately 80-Hz. The source of DC power for amplifiers A1, A2 is an approximately +3.6-V source VAN, which is produced by power supply/control 32 (refer to FIG. 1), suitably limited for the protection of amplifiers A1, A2 by a Schottky diode D1. The output signal ECG of amplifier A2 is input to ADC 22 (refer to FIG. 1) after further filtering.

Another output of amplifier A1 is AC-coupled by a 0.1-μF capacitor C3 to ICDM pulse detector 20b. This signal, which represents the amplified, but unfiltered ECG voltage between electrodes 18a, 18b, becomes one input of a window comparator circuit comprising comparators A3, A4, and resistors R8 through R12. Resistors R8 and R9, which in the preferred embodiment are 81-kμ and 4.7-Mμ, respectively, divide the voltage present on the resistor R8-side of coupling capacitor C3 in a suitable ratio that establishes, via DC bias voltage V/2 (preferably approximately +1.2-V), the voltage levels of two of the inputs to comparators A3, A4. The other inputs to comparators A3, A4 are established by a +3-V (+3V) voltage divider network including resistors R10, R11, and R12, which in the preferred embodiment are 150-kΩ, 75-kΩ and 100-kΩ, respectively. These bias voltage and resistor values are chosen in accordance with the preferred embodiment to establish a lower threshold level of approximately −1.2-V and an upper threshold level of approximately +1.6-V, which have been found to provide ICDM pulse detector 20b with window comparator circuit means for discriminating an ICDM pulse from a QRS complex, noise, motion or other artifacts, thus providing apparatus 10 with the ability to detect ICDM pulses, but to reject QRS complexes, and motion and other artifacts. The outputs of comparators A3, A4 are "wired-OR" connected and biased, via a 10-kΩ resistor R13, to produce the low-active TRIGGER- signal to microcontroller 12 (refer to FIG. 1).

Those skilled in the art will appreciate that, so long as the amplified ECG signal voltage input to ICDM pulse detector 20b remains within the voltage limits set by the voltage divider network comprising resistors R10, R11, R12, TRIGGER- remains high (inactive). If the amplified ECG signal voltage input exceeds the predefined limits, by too high or too low an excursion within the frequency response of comparators A3, A4, then TRIGGER- goes low (active), thereby signalling microcontroller 12 that an implanted ICDM-produced pulse may have occurred. Thus, the amplitude of the ECG signal is window-compared by ICDM pulse detector 20b to amplitude criteria that characterize ICDM devices. In response to a TRIGGER- input on its control line, microcontroller 12 measures the period of time $T_{TRIGGER-}$ that the TRIGGER- signal is low (active) to determine whether the candidate pulse meets predetermined duration criteria that characterize ICDM devices. In accordance with the preferred method and apparatus of the invention, if TRIGGER- is low (active) for between approximately 5-ms and 12.8-ms, then an ICDM-produced pulse is determined to have occurred. Otherwise, the TRIGGER- signal is assumed to have been an artifact, e.g. electrostatic discharge. Thus, ICDM pulse discriminating means includes window comparator and programmed microcontroller means for comparing amplitude, frequency and duration characteristics of the voltage across a region of the patient's skin predetermined characteristics.

Figure 3A:
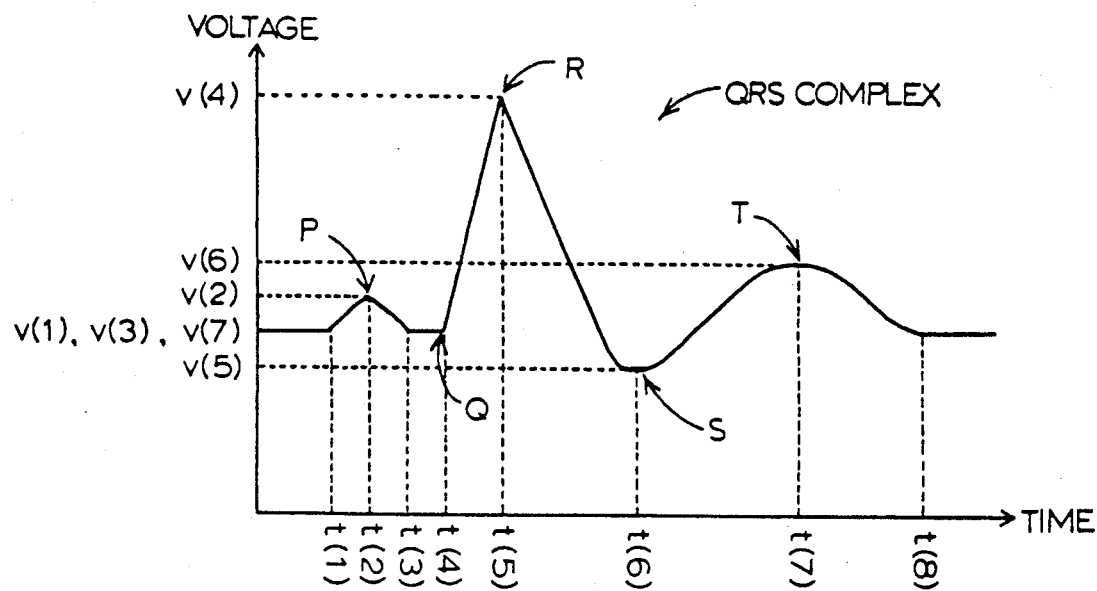
FIGS. 3A and 3B are a graph of a typical QRS complex and a graph of a typical ICDM pulse, which graphs are useful in understanding the operation of the ICDM pulse detection means illustrated in FIG. 2.
Figure 3B:
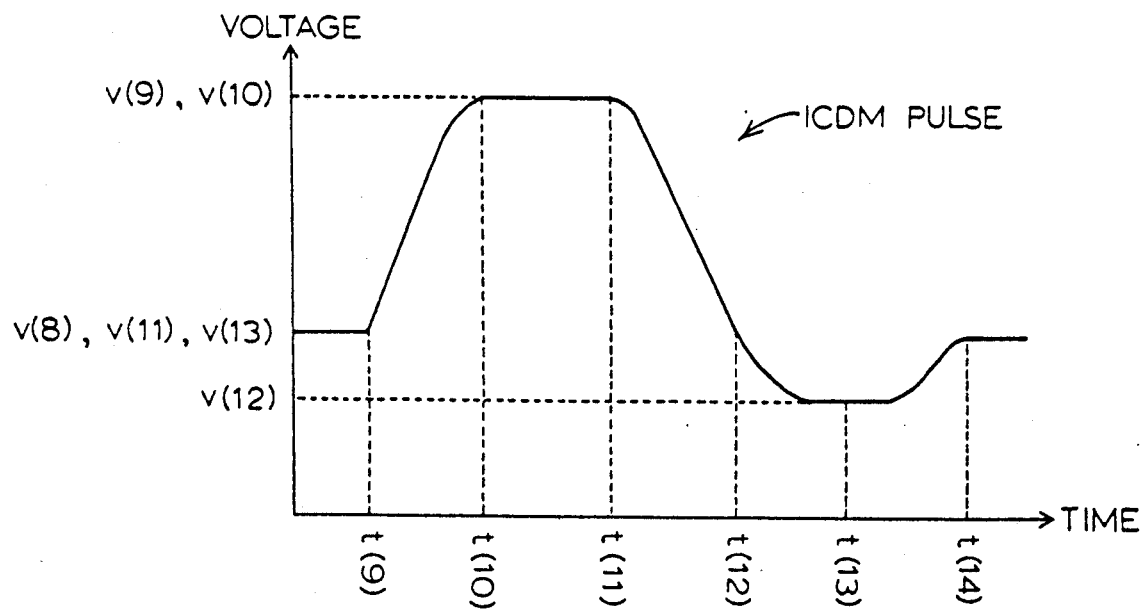

Referring to FIGS. 3A and 3B, the important amplitude and duration attributes of ECG signals and ICDM-produced pulses will be described. FIG. 3A illustrates a typical QRS complex, with its various inflection points, which are of little importance to the present invention, indicated at Cartesian coordinates (t(2),v(2)), (t(3),v(3)), (t(4),v(3)), (t(5),v(4)), (t(6),v(5)) and (t(7),v(7)). FIG. 3B illustrates a typical ICDM pulse.

Note that the waveforms illustrated in FIGS. 3A and 3B have very different amplitude and frequency characteristics. For example, the total excursion of a typical QRS complex, e.g. v(4)-v(5), is only a few millivolts, while the total excursion of a typical ICDM pulse, e.g. v(9)-v(12) or v(10)-v(12), is several volts. Conversely, the elapsed time envelope of a typical QRS complex, e.g. t(8)-t(1), approaches one hundred milliseconds, while the elapsed time envelope of a typical ICDM pulse, e.g. t(13)-t(9), is only a few milliseconds. Of course, both signal waveforms, which have common baseline voltages v(1), v(3), v(7) (refer to FIG. 3A) and v(8), v(13) (refer to FIG. 3B), typically will appear at the inputs of ECG filter/ICDM detector 20 when electrodes 18a, 18b are in contact with the skin of a patient having an implanted ICDM (refer to FIG. 1). Thus, they must be discriminated from one another, in order to determine the patient's cardiac condition immediately preceding, and immediately following, a ICDM-produced pulse. Moreover, they must be discriminated from noise, motion, electrostatic discharge and other artifacts.

Referring still to FIG. 3B, other important amplitude and duration attributes of a typical ICDM pulse are described. The typical ICDM pulse is of generally trapezoidal shape during its several volt, positive excursion v(9)-v(8) from t(9) to t(12), and has a relatively flat peak from t(10) to t(11). During its capacitor discharge-produced, several hundred millivolt, negative excursion v(11)-v(12) from t(12) to t(14), the typical ICDM pulse also is of generally trapezoidal shape, as shown. The apparatus of the invention in its preferred embodiment takes advantage of the fact that the positive pulse of most ICDM devices is much greater than +1.6-V in amplitude and that the entire pulse of most ICDM devices is within the range of 6-ms to 12-ms in duration. It is these ICDM pulse amplitude and duration attributes, which have been determined to be common among all known, implanted ICDM devices, that renders it possible for apparatus 10 accurately and reliably to detect an ICDM-produced pulse. Within the spirit of the invention, ICDM pulses having other attributes can be detected, by simply changing the voltage threshold levels of ICDM pulse detector 20b, or by changing the parameters by which microcontroller 12 determines whether TRIGGER- was low (active) for a characteristic period of time.

In accordance with the preferred method and apparatus of the invention, microcontroller 12 continuously samples the digitized ECG data from ADC 22, and stores it in successive scrolling storage buffers each of limited depth within RAM 16. By scrolling is meant the well-known manner in which memory is managed by writing successive bytes of data until a buffer is filled, and thereafter continuing to write successive bytes of data as the oldest bytes previously written into the buffer are successively lost, thereby creating a temporal memory 'window' that always represents the most recently acquired data. In other words, a scrolling storage buffer may be thought of as a storage buffer that is circularly indexed, or circularly addressed by a pointer. Its hardware analogue is a shift register, and within the spirit of the invention, it may be so-implemented. Thus, a particular scrolling buffer within RAM 16 contains, at any instant in time, digitized ECG data representing the patient's most recent cardiography.

Concurrently with its continuous sampling an recording of ECG data, microcontroller 12 also continuously monitors its control input to which the TRIGGER- signal is connected, thereby to monitor, via ICDM pulse detector 20b, the voltage between electrodes 18a, 18b. Upon its determination that a ICDM-produced pulse has occurred, i.e. a pulse meeting the duration criteria described above, microcontroller 12 initiates a timeout. The predetermined duration of the timeout is generally less than, and preferably approximately equal to one-half of, the time required nominally to fill the buffer, i.e. one-half the time it would take once to update the buffer, based upon the ECG data sampling rate. After initiating the timeout, microcontroller 12 continues, for the duration of the timeout, to record ECG data into the scrolling buffer. When the timeout ends, i.e. when the predetermined period of time lapses, microcontroller 12 halts the continuous recording of ECG data into the scrolling buffer, thereby capturing ("capture-storing") the recorded ECG data for subsequent playback. Microcontroller 12 then initializes a new scrolling buffer, and repeats the ECG data-sampling, recording and TRIGGER-monitoring steps with such new buffer.

The apparatus of the invention in its preferred embodiment now will be summarized. Operatively connected ECG data sampling and recording means for measuring the voltage across a region of the patient's skin and for producing a ECG data record representative thereof includes electrodes 18a, 18b; ECG amplifier/filter 20a; and ADC 22 (referred to herein as sampling means); and microcontroller 12; ROM 14; and RAM 16 (referred to herein as recording means). The sampling and recording means produces such a data record over a continuously advancing period of time of predetermined duration, by the management of scrolling storage buffers of finite depth within RAM 16, into which the ECG data is recorded by microcontroller 12, which executes instructions stored in ROM 14. In other words, each buffer represents ECG data sampled over a given period of time that corresponds with the depth of the buffer and the ADC sampling rate, and each buffer is continuously updated for a period of time. Detection means, or ICDM pulse detector 20b, connected with electrodes 18a, 18b, senses an ICDM pulse produced by an implanted ICDM, and produces a TRIGGER- signal upon the occurrence of a pulse meeting predefined amplitude and frequency criteria. Finally, means operatively connected with the sampling and recording means and responsive to the TRIGGER- signal, or microcontroller 12 operating in response to a TRIGGER- signal meeting predefined duration criteria, times out, halts the recording of ECG data by the recording mean into the buffer and then selects other such buffers for capture-storing ECG data, in response to subsequent ICDM pulse occurrences. Thus, apparatus 10 selectively captures ECG data recorded near in time to occurrences of ICDM-produced pulse TRIGGER- signals.

In accordance with the preferred embodiment of the invention, means responsive to the detection means for validating the occurrence of a ICDM-produced pulse is provided by microcontroller 12's measuring the duration of TRIGGER- signal's low (active) period and comparing it to duration criteria, e.g. 5-ms $T_{TRIGGER-} \leq 12.8$-ms. In accordance with the preferred embodiment, the halting means includes a timeout mechanism which operates to halt the recording means for a period of time corresponding to a predetermined number of ECG data samples after the occurrence of each TRIGGER- signal. This ensures that both pre-TRIGGER- and post-TRIGGER- signal ECG data are captured within the 'windows' of RAM 16 reserved for the scrolling storage buffers. In accordance with the preferred embodiment, the predetermined number of ECG data samples following a TRIGGER- signal (or the predetermined period of time corresponding thereto) after which the recording means is halted is programmable, thereby accommodating individual patient idiosyncracies or physician preferences. Also in accordance with the preferred embodiment of the invention, means for indicating the times of the occurrences of such ICDM-produced pulses, relative to the corresponding predetermined period of time represented by the capture-stored ECG data, is provided by microcontroller 12's marking of each capture-store buffer by a flag or other indication of the location in the ECG data buffer corresponding to the trigger event. It will be appreciated that such indicating means, or marking, may be implemented in a variety of ways, including the setting of an otherwise unused bit (e.g. a flag) in a byte or word of an ECG data sample.

Those of skill in the art will appreciate that, although it is of necessarily limited capacity in lightweight, self-contained, ambulatory apparatus, RAM 16 nevertheless provides for the capture-store of significant ECG data: that which is related in time to the occurrence of a ICDM-produced pulse. By managing a number of scrolling buffers as described above, microcontroller 12 provides for the capture-store of selected ECG data of particular interest to the diagnostician in treating a patient having an implanted ICDM. It will be appreciated that the predetermined period of time following a TRIGGER- signal after which microcontroller 12 halts ECG data recording and captures an ECG data 'window' may be adjusted to provide the most desirable timing relationship therebetween. For this reason, the parameters that determine the timeout used by microcontroller 12 are programmable, in accordance with the preferred embodiment of the invention. Those of skill will appreciate that this programmability may be accomplished by any of a number of well-known means. For example, the parameters may be stored in the writable control store region of a ROM, or may be switch-selectable to be read into RAM, so that a subscribing physician may take account of an individual ICDM patient's particular cardiology. In accommodation of such flexibility, and in accordance with the preferred method and apparatus of the invention, microcontroller 12 indicates the important timing relationship between each ICDM pulse TRIGGER- and the ECG data capture-stored in response thereto. It does so by marking each buffer with a flag the location of which indicates the time of the occurrence of the ICDM pulse to which it corresponds.

In accordance with the preferred embodiment of the invention, the user of apparatus 10 may also manually trigger the capture-store of ECG data, e.g. by selecting a pushbutton on keyboard 36 (refer to FIG. 1). In response, microcontroller 12 specially indicates, e.g. by marking the buffer, that the capture-store represented thereby was at the behest of the user of apparatus 10, rather than being an automatic result of a detected ICDM-produced pulse. Skilled persons will appreciate that, within the spirit of the invention, many modifications may be made to the disclosed means and manners of selectively capture-storing and marking ECG data.

The preferred method of the invention now is understood, by reference to the preferred embodiment described above. It comprises continuously sampling ECG data and recording the same in semiconductor memory means having limited capacity, e.g. by the sampling and recording means; concurrently monitoring the voltage between each of at least a pair of electrodes in operative contact with the patient's skin to produce a trigger signal indicative of the occurrence of a ICDM-produced pulse, e.g. by the detection means; continuing for a predetermined period of time after the trigger signal is produced to record ECG data in such memory means, e.g. by the microcontroller initiating a timeout but continuing to record data; and thereafter halting the continuous recording, e.g. by the microcontroller responding to the timeout lapse by stopping to select a new buffer, thereby to capture selectively such recorded ECG data in such memory means for subsequent playback. Generally, the continuing step is for a predetermined period of time that is less than, and preferably approximately one-half of, the time nominally required to fill such memory means with ECG data. A further step of marking, in such memory means, the time of occurrence of the ICDM-produced pulse relative to the captured ECG data recorded in the memory means enables the cardiographic condition of the patient to be correlated with the ICDM pulse that resulted from, and/or affected the condition.

Another way of describing the preferred method of the invention in the long-term, selective recording of a patient's cardiac response to an implanted ICDM is as follows. First, the sampling and recording means continuously records ECG data by sampling the voltage waveform between each of a pair of skin electrodes attached to an ambulatory patient, comparing the ECG data to predetermined QRS complex criteria (e.g. by the operation of the ECG amplifier/filter and, optionally, by the operation of the microcontroller in conventionally analyzing, qualifying and/or interpreting the sampled data) and storing QRS complex data in a storage buffer of finite depth. Second, the detection means and microcontroller 12 continuously monitor an implanted ICDM by sampling the voltage waveform between each of the same pair of electrodes, comparing the voltage to predetermined ICDM pulse criteria (e.g amplitude and frequency criteria by the detection means and duration criteria by the microcontroller) and indicating the occurrence of a ICDM pulse in timed relation to the stored QRS complex data (e.g. marking by the microcontroller). Third, the recording means and the microcontroller continue the recording step for a first predetermined period of time after the indicating (e.g. one-half the time it takes once to fill a scrolling buffer of defined, limited depth). Fourth, the microcontroller halts the recording step to capture selectively that stored QRS complex data in the scrolling buffer which represents ECG data sampled during a second predetermined period of time (e.g. the entire time required once to fill such scrolling buffer), which second predetermined period of time includes the time of said indicating of the occurrence of the ICDM pulse. Fifth, the microcontroller selects another such scrolling storage buffer for subsequent selective ECG data recording (e.g. by initializing it and its address pointer(s)). Finally, the apparatus of the invention repeats the first, continuously recording, step with such other buffer (under the control of the microcontroller).

Those of skill in the art will appreciate that the various means and steps of the preferred embodiment and method maY be accomplished in other ways. For example, apparatus 10 may be implemented in hardware, alone or in combination with firmware or software. The detection means may be implemented entirely in software, e.g. by the provision of another ADC in parallel with ADC 22, or entirely in hardware, e.g. by the provision of ICDM pulse detector 20b with a timing circuit capable of window-comparing the duration of a low (active) TRIGGER- signal with a minimum and a maximum value. Certain of the steps of the preferred method may be combined, or reordered, to effect substantially the same, desired effect of selectively recording ECG data in the memory means of an ambulatory device capable also of detecting a ICDM-produced pulse, and treating the pulse as a trigger event that prompts the capture-store of the ECG data for subsequent playback.

Accordingly, while a preferred method for practicing the invention, and a preferred embodiment of the apparatus of the invention, have been described herein, it is appreciated that further modifications are possible that come within the scope of the invention.

It is claimed and desired to secure by letters patent:

1. For non-invasive monitoring of a patient having an implanted defibrillator, an externally worn ambulatory heart monitoring apparatus comprising:

ECG data sampling and recording means, said sampling means for sampling the voltage across a region of the patient's skin and including at least a pair of electrodes for measuring the voltage across a region of the patient's skin and said recording means for producing an ECG data record representative thereof over a continuously advancing period of time of predetermined duration;

detection means including comparing means operatively connected with said electrode pair for detecting a defibrillation pulse produced by an implanted defibrillator, and for comparing the sampled voltage to predetermined criteria, said detection means produced a trigger signal upon the occurrence of such a pulse; and means operatively connected with said sampling and recording means and responsive to said trigger signal of selectively capturing ECG data recorded near in time to the occurrence of said trigger signal.

2. The apparatus of claim 1 wherein said detection means includes means for discriminating such a pulse from a QRS complex.

3. The apparatus of claim 2 wherein said discriminating means includes means for comparing amplitude and frequency characteristics of the voltage with predetermined criteria.

4. The apparatus of claim 1 wherein said detection means includes means for discriminating such a pulse from noise, motion, electrostatic discharge or other artifacts.

5. The apparatus of claim 4 wherein said discriminating means includes means for comparing amplitude and frequency characteristics of the voltage with predetermined criteria.

6. A method for monitoring and recording indicia of the performance of the heart of a patient equipped with an implanted defibrillator comprising:

continuously sampling ECG data and recording the same in semiconductor memory means having limited capacity;

monitoring, concurrently with said ECG data recording, the voltage between each of at least one pair of electrodes in operative contact with the patient's skin to produce a trigger signal indicative of the occurrence of a defibrillator-produced pulse;

continuing, for a predetermined period of time after such a trigger signal is produced, to record ECG data in such memory means; and thereafter halting said continuous recording to capture selectively such recorded ECG data in such memory means for subsequent playback.

7. The method of claim 6, which further comprises the step of marking in such memory means the time of the occurrence of a defibrillator-produced pulse relative to the captured ECG data recorded therein.

8. The method of claim 7, wherein said continuing step is for a predetermined period of time that is generally less than the time required nominally to fill such memory means with ECG data, thereby capturing both pre-trigger and post-trigger signal ECG data.

9. For the long-term, selective recording of a patient's cardiac response to an implanted defibrillator, a method comprising:

(a) continuously recording ECG data by sampling the voltage waveform between each of a pair of skin electrodes attached to an ambulatory patient, comparing such ECG data to predetermined QRS complex criteria and storing QRS complex data in a storage buffer of finite depth;

(b) continuously monitoring an implanted defibrillator by sampling the voltage waveform between each of such pair of skin electrodes, comparing such voltage to predetermined defibrillation pulse criteria and indicating the occurrence of a defibrillation pulse in timed relation to such stored QRS complex data;

(c) continuing said recording for a first predetermined period of time after said indicating;

(d) halting said recording to capture selectively that stored QRS complex data in such buffer which represents ECG data sampled during a second predetermined period of time including the time of said indicating;

(e) selecting another storage buffer of finite depth for subsequent selective ECG data recording; and (f) repeating step (a) with such other buffer.

10. For use by a patient having an implanted defibrillator, ambulatory heart monitoring apparatus comprising:

sampling means including at least a pair of electrodes for measuring the voltage across a region of the patient's skin and for producing ECG data representative thereof over a continuously advancing period of time of predetermined duration;

recording means operatively connected with said sampling means for recording ECG data, said recording means including plural scrolling storage buffers, each of finite depth into which such ECG data is selectively recorded;

detection means operatively connected with said pair of electrodes for sensing a defibrillation pulse produced by an implanted defibrillator, said detection means producing a trigger signal upon the occurrence of such a pulse that meets predefined amplitude and frequency criteria;

halting means operatively connected with said recording means and responsive to said trigger signal for halting the operation of said recording means, thereby to selectively record in a selected buffer selected ECG data that are sampled by said sampling means near in time to the occurrence of said trigger signal; and mean for selecting another scrolling storage buffer for captured storage of selected ECG data in response to subsequent defibrillation pulse occurrences.

11. The apparatus of claim 10, which further comprises means for indicating the times of the occurrences of such defibrillator-produced pulses relative to the corresponding predetermined period of time represented by the capture-stored ECG data.

12. The apparatus of claim 11, wherein said halting means includes a timeout mechanism which operates on said recording means for a period of time corresponding to a predetermined number of ECG data samples after the occurrence of said trigger signal, thereby to capture-store both pre-trigger and post-trigger signal ECG data.

* * * * *